United States Patent [19]
Greenfield et al.

[11] 4,129,448
[45] Dec. 12, 1978

[54] FORMALDEHYDE STABILIZED COATING COMPOSITIONS

[75] Inventors: Stanley A. Greenfield, Ambler; John A. Dupont, Glenside, both of Pa.

[73] Assignee: Rohm and Haas Company, Philadelphia, Pa.

[21] Appl. No.: 830,716

[22] Filed: Sep. 6, 1977

Related U.S. Application Data

[63] Continuation-in-part of Ser. No. 389,745, Aug. 20, 1973, abandoned.

[51] Int. Cl.$^2$ ............................................... C09D 5/14
[52] U.S. Cl. ...................... 106/15 R; 260/29.6 N; 260/29.6 MN; 260/29.6 MQ; 428/245
[58] Field of Search .................. 106/15 AF, 15 R; 260/29.6 MQ, 29.6 MN

[56] References Cited
U.S. PATENT DOCUMENTS

| 3,523,121 | 8/1970 | Lewis et al. | 260/306.7 |
| 3,761,488 | 9/1973 | Lewis et al. | 260/302 |

OTHER PUBLICATIONS

Walker, J. Frederic, Formaldehyde ACS Monograph Series, No. 159 (Third Edition), Reinhold, N.Y., 1964 Chpt. 20, pp. 569–574.

*Primary Examiner*—Lucille M. Phynes

[57] ABSTRACT

Coating compositions which contain a mildew-controlling amount of an isothiazolone are stabilized against chemical decomposition of the isothiazolone by the addition of formaldehyde or a compound which releases formaldehyde under basic conditions.

21 Claims, No Drawings

FORMALDEHYDE STABILIZED COATING COMPOSITIONS

CROSS REFERENCE TO RELATED APPLICATION

This application is a continuation-in-part of our pending application U.S. Ser. No. 389,745 filed on Aug. 20, 1973, now abandoned.

THE DISCLOSURE

This invention relates to isothiazolone-containing coating compositions, particularly paints, in which the isothiazolone is stabilized against chemical decomposition and from which coatings with improved mildew resistance are obtained.

Coating compositions, and particularly latex paints, are often formulated at relatively high pH to improve their mechanical stability, freeze-thaw stability, and dispersion stability. However, 3-isothiazolones, which have been found to be excellent mildewcides, can undergo chemical decomposition under highly basic conditions, thus, decreasing their effectiveness in controlling mildew in the final coating. It has now been found that the chemical decomposition of the isothiazolone in these coating compositions can be effectively minimized by the addition of formaldehyde or a suitable formaldehyde-releasing agent to the compositions. By stabilizing the coating compositions against chemical decomposition of the isothiazolone, the coatings produced from these compositions have improved mildew resistance.

According to the invention, a coating composition which comprises a film-forming material, a carrier, which may be a solvent, and a mildew-controlling amount of a 3-isothiazolone is stabilized against chemical decomposition of the isothiazolone by incorporating into the composition a stabilizing amount of formaldehyde or of a compound which releases formaldehyde under basic conditions. Generally, the 3-isothiazolone has the formula

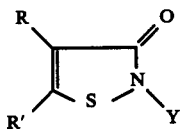

(I)

wherein
Y is a hydrogen atom, a ($C_1$-$C_{18}$)alkyl group, a ($C_6$-$C_{10}$)aryl group, or a ($C_7$-$C_{10}$)aralkyl group,
R is a hydrogen atom, a halogen atom, or a ($C_1$-$C_4$)alkyl group,
R' is a hydrogen atom, a halogen atom, or a ($C_1$-$C_4$)alkyl group, or
R and R' can be taken together to complete a benzene ring, optionally substituted with one or more halogen atoms, nitro groups, ($C_1$-$C_4$)alkyl groups, cyano groups, ($C_1$-$C_4$)alkoxy groups, or the like.

The Y substituents as defined above include both unsubstituted alkyl, aryl, and aralkyl groups as well as alkyl, aryl, and aralkyl groups substituted with one or more halogen atoms, ($C_1$-$C_4$)alkoxy groups, nitro groups, cyano groups, carboxy groups, carb($C_1$-$C_4$)alkoxy groups, or the like.

Any compound which will act as a formaldehyde-releasing agent under basic conditions as well as formaldehyde can be used in the coating compositions of the invention. Among the suitable formaldehyde-releasing agents are certain quaternary salts of hexamethylenetetramine, including 1-(3-chloroallyl)-3,5,7-triaza-1-azoniaadamantane chloride, 1-(3-propyne)-3,5,7-traiza-1-azoniaadamantane chloride, 1-tolyl-3,5,7-traiza-1-azoniaadmantane chloride, and the like. When formaldehyde is used, it is generally added to the coating composition dissolved in the same solvent as the carrier for the composition. For example, formaldehyde can be added to aqueous polymer emulsions in water solution.

The formaldehyde or formaldehyde-releasing agent can be added to the compositions of the invention in any concentration which will effect the desired stabilization of the 3-isothiazolone. Generally, the formaldehyde or formaldehyde-releasing agent will be present in a concentration equivalent to about 0.25 to about 20 pounds, and preferably about 2 to about 5 pounds, of 37% aqueous formaldehyde per 100 gallons of paint. Higher levels of formaldehyde can be used but are generally economically impractical.

In acrylic emulsion polymer systems, the formaldehyde or formaldehyde-releasing agent is used in conjunction with ammonia or an organic amine to produce a neutralized buffered coating composition having good physical stability as well as chemical stability of the 3-isothiazolone. Generally, the pH of such a coating composition will be about 6.0 to about 9.2, and preferably about 8.6 to about 9.1, depending, for example, on the particular emulsion or coating formulation involved. In forming the coating composition, a molar excess of formaldehyde or formaldehyde-releasing agent is preferable. Generally, about ¼ to about 20, and preferably about 1 to about 2 pounds of 28% aqueous ammonia or organic amine per 100 gallons of paint will be used with about ½ to about 20, and preferably about 2 to about 5 pounds, of 37% aqueous formaldehyde per 100 gallons of paint. Higher levels of formaldehyde and ammonia or amine can be used but are generally economically impractical. Among the organic amines which can be used to produce the neutralized buffered coating compositions are dimethylaminoethanol, t-butylaminoethanol, triethylamine, morpholine, monoisopropanolamine, aminomethylpropanol, N-methyl-2-pyrrolidone, as well as similar amines which are used to neutralize acrylic emulsions for coating purposes.

The coating compositions of the invention contain at least one 3-isothiazolone. The 3-isothiazolones of Formula I can be prepared by the methods disclosed in U.S. Pat. Nos. 3,849,430, granted on Nov. 19, 1974, No. 3,761,488, granted on Sept. 25, 1973, and Ser. No. 855,046, filed on Sept. 3, 1969, now abandoned, and in U.S. Pat. No. 3,517,022, of Miller et al., granted on June 23, 1970. Generally, the isothiazolones of Formula I in which R and R' do not form a benzene ring are prepared by the oxidative cyclization of a disulfide-amide having the formula

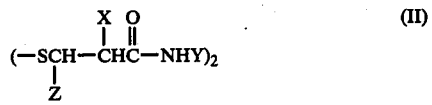

(II)

or, a mercapto-amide having the formula

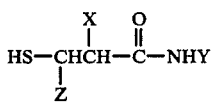

wherein X and Z are hydrogen or lower alkyl and Y is as defined above. The cyclization is accomplished by contacting the amide with a halogenating agent. Typical halogenating agents include chlorine, bromine, sulfuryl chloride, sulfuryl bromide, N-chlorosuccinimide, N-bromosuccinimide, and the like. Chlorine and sulfuryl chloride are the preferred halogenating agents. The benzisothiazolones of Formula I are prepared by the reaction of a primary amine with an o-halosulfenylbenzoyl halide or the intramolecular condensation of an o-halosulfenylbenzamide.

The concentration of isothiazolone which is added to the paint can vary over a wide range depending on such factors as the type of paint involved, the locality of application, and the type of surface on which the paint is applied. Generally, about 0.1 pounds to about 20 pounds of isothiazolone per 100 gallons of paint will be effective. The preferred range of incorporation is about 0.5 to about 12 pounds of isothiazolone per 100 gallons of paint. Mixtures of the isothiazolones can also be used. Among the particularly useful isothiazolones are those in which Y in Formula I is an alkyl group, in which the alkyl group can have a branched-or straight-chain spatial configuration, including 2-butyl-3-isothiazolone, 2-hexyl-3-isothiazolone, 2-octyl-3-isothiazolone, 2-nonyl-3-isothiazolone, 2-decyl-3-isothiazolone, 2-dodecyl-3-isothiazolone, and the like, and their 5-halo analogues.

Any coating composition which contains a 3-isothiazolone can also comprise formaldehyde or a suitable formaldehyde-releasing agent, including oil-based paints, waterbased paints formulated at any pH, lacquers, non-aqueous dispersions, and other decorative or protecting coating compositions. Coating compositions containing formaldehyde or a formaldehyde-releasing agent are particularly useful in formulating coatings which provide gloss or semi-gloss finishes.

In a preferred embodiment of the invention, the coating composition is an aqueous dispersion of a vinyl or acrylic emulsion polymer, such as those used in making waterbased paints. Examples of such dispersions include homopolymers and copolymers, of: (1) vinyl esters of an aliphatic acid having 1 to 18 carbon atoms, especially vinyl acetate; (2) acrylic acid esters and methacrylic acid esters of an alcohol having 1 to 18 carbon atoms, especially methyl acrylate, ethyl acrylate, butyl acrylate, 2-ethylhexyl acrylate, methyl methacrylate, ethyl methacrylate and butyl methacrylate; and (3) mono- and di-ethylenically unsaturated hydrocarbons, such as ethylene, isobutylene, styrene, and aliphatic dienes, such as butadiene, isoprene, and chloroprene.

Poly(vinyl acetate) and copolymers of vinyl acetate with one or more of the following monomers: vinyl versatate or other vinyl esters of fatty acids having 3 to 18 carbon atoms, vinyl chloride, vinylidene chloride, styrene, vinyltoluene, acrylonitrile, methacrylonitrile, mono- or difumaric or -maleic acid esters, such as of the alkanols having 1 to 4 carbon atoms, including for example, monomethyl fumarate, diethyl maleate or fumarate, dibutyl maleate or monobutyl maleate, or one or two of the acrylic and methacrylic acid esters mentioned above are often used as the film-forming component of aqueous base paints. Similarly, copolymers of one or more of the acrylic or methacrylic acid esters mentioned above with one or more of the following monomers: vinyl acetate, vinyl esters of higher fatty acids, the mono- or di-alkyl esters of itaconic acid, the mono- or di-alkyl esters of fumaric acid or the mono- or di-alkyl esters of maleic acid, such as the esters of methanol, ethanol, or butanol, vinyl chloride, vinylidene chloride, styrene, vinyltoluene, acrylonitrile, and methacrylonitrile are also commonly employed in aqueous base paints. Homopolymers of ethylene or isobutylene, and copolymers of one or more of these hydrocarbons or of styrene with one or more esters, nitriles, or amides of acrylic acid or of methacrylic acid or with vinyl esters, such as vinyl acetate and vinyl chloride, or with vinylidene chloride are also used. The diene polymers are generally used in aqueous base paints in the form of copolymers with one or more monomers following: styrene, vinyltoluene, acrylonitrile, methacrylonitrile, and the above-mentioned esters of acrylic acid or methacrylic acid. It is also quite common to include a small amount, such as about ½ to 8% or more, of an acid monomer in the monomer mixture used for making the copolymers of all three general types mentioned above by emulsion polymerization. Acids used include acrylic, methacrylic, itaconic, aconitic, citraconic, crotonic, maleic, fumaric, the dimer of methacrylic acid, and the like.

Particularly useful coating compositions are the copolymers of (a) a soft acrylate, such as a $(C_1-C_8)$alkyl acrylate (especially methyl acrylate, ethyl acrylate, butyl acrylate, 2-ethylhexyl acrylate or mixtures thereof), with (b) at least one hard comonomer, such as methyl methacrylate, acrylonitrile, styrene, vinyltoluene, vinyl acetate, and vinyl chloride, and (c) about 0.5 to 8% by weight of an $\alpha,\beta$-monoethylenically unsaturated acid, such as acrylic, methacrylic, crotonic, or itaconic acid such as those described in Conn et al. U.S. Pat. No. 2,795,564, June 11, 1957; and blends of any of these polymer dispersions with each other or with similar polymers containing a polar group, such as any of the blends mentioned in Scott U.S. Pat. No. 3,356,627, Dec. 5, 1967.

These aqueous dispersions can be made using one or more emulsifiers of anionic, cationic, or nonionic type. Mixtures of two or more emulsifiers regardless of type can be used, except that it is generally undesirable to mix a cationic with an anionic type in any appreciable amounts since they tend to neutralize each other. The amount of emulsifier can range from about 0.1 to 6% by weight or sometimes even more, based on the weight of the total monomer charge. When using a persulfate type or, in general, an ionic type of initiator, the addition of emulsifiers is often unnecessary and this omission or the use of only a small amount e.g. less than about 0.5% of emulsifier, may sometimes be desirable from the cost standpoint (elimination of expensive emulsifier), and less sensitivity of the dried coating or impregnation to moisture, and, hence, less liability of the coated substrate to be affected by moisture, which, for instance, would produce coatings less liable to swelling or softening, particularly when subjected to humid atmospheres. The average particle size or diameter of these dispersed polymers is generally from about 0.03 to 3 microns or even larger.

The compositions of the invention can contain additional materials of various kinds besides the polymeric vehicle to vary the properties and to adapt the compositions for various uses. For example, plasticizers can be added. In making paints, incorporation of pigments and/or dyes is important. The relative proportions of vehicle to pigment may fall in a wide range, such as from a ratio of 1:20 to 20:1 but for most purposes is from 1:5 to 5:1. Pigments can be dispersed in the paint vehicle by any of the well-known techniques of pigment dispersion in paint formulation. In water-based paints, the surfactant for dispersing the pigment composition may be the same or different from the stabilizing surfactants of the polymer vehicle. Ordinarily a concentration of up to 2% of the auxiliary pigment-dispersing surfactant based on the weight of the pigment composition is adequate, the preferred concentration being 0.1% to 1% on the indicated basis. It is preferred that the total amount of pigment dispersing surfactant and the stabilizing surfactants of the respective latices does not exceed 10% based on the total weight of the vehicle.

Water-soluble cellulose derivatives such as methyl cellulose, carboxymethyl cellulose or hydroxyethyl cellulose, especially methyl cellulose, can be used for bodying purpose in water-based paints. These materials are used in their ordinary small effective proportions.

Another desirable ancillary component which is preferentially present in aqueous dispersion paint compositions is a volatile water-soluble organic anti-freeze agent to provide the aqueous paint with freeze-thaw stability. Ethylene glycol is especially useful for this purpose at concentrations up to about 5% by weight of the total composition. Other glycols and polyglycols can be used for this purpose.

Aqueous dispersion paint compositions containing surfactants ordinarily foam unless selection of the dispersants is specifically directed to the inherently non-foaming species. Anti-foam agents can be included in aqueous paint formulations to minimize foaming. High boiling alcohols, polyglycols, silicone liquids and other anti-foam agents well-known to the coating art can be included in the composition as an ancillary component.

For coating compositions which are adequately flexible, esternal plasticization of the polymer vehicle is ordinarily unnecessary. However, ancillary plasticizer can be included in the compositions in a minor proportion up to 10% by weight of the polymer vehicle, preferably no more than 5%. Non-volatile ester plasticizers, for example, the phosphates, such as tricresyl phosphate, and the phthalates, such as dibutyl phthalate, or the polymeric polyester or alkyd plasticizers can be used.

The total non-volatile content of the coating compositions, ordinarily designated as the solids content, can vary widely. Often, it is desirable that the non-volatile content be at least 30% by weight in order that a practical amount of the film-forming material per coat is applied. The coating compositions often can be satisfactorily formulated in a non-voltile content as great as 70%, but at this concentration thinning may be necessary for satisfactory application. The preferred non-volatile content is from about 40% to 60% by weight.

The viscosity of the coating compositions also can be varied widely. A Stormer viscosity of about 70 to 100 K. U. at 25° C. is a desirable ready-to-apply brush consistency. This is not a critical characteristic as the coating composition can be further modified satisfactorily with thixotropy controlling agents to provide the composition with non-drip characteristics with adequate brushout characteristics.

Other auxiliary materials that may be used include: dispersing agents for dispersing and maintaining in a finely divided state the pigments, colors, or extenders, such as aromatic sulfonates condensed with formaldehyde or any of the suitable commercial dispersing agents such as complex alkali metal phosphates or ethylene polyaminoacetates, defoaming agents, including waxes, oils, or mineral spirits, or an alkylphenoxyethanol, fatty acid amides, phosphate esters, or a solution of an amine or amide in an oil; humectants, such as water-soluble gums, glycol laurate, propylene glycol, diethylene glycol, and the like, thickeners, such as water-soluble gums, water-soluble cellulose ethers, including hydroxyethyl cellulose, water-dispersed starches and proteins, and the like; perfume-like materials, including neutralizing and masking agents, which are used to overcome odors or to impart pleasant and distinctive odors; other resinous materials in dispersed form, such as alkyl resins, drying oils, or latices of styrene or of styrene and butadiene to cheapen and extend the binders of this invention, and auxilialry corrosion-inhibiting agents, such as sodium benzoate, guanyl urea phosphate, or sodium nitrite, in an amount of 0.05% to 5%, and most commonly 0.1% to 2% of the dispersed copolymer etc.

The compositions of the present invention may be of strictly thermoplastic character or they may be of thermosetting character. The compositions may comprise auxiliary components which impart thermosetting qualities to the composition. For example, there may be added an aldehyde, such as the resin-forming condensates of formaldehyde with phenol, urea, N,N'-ethyleneurea, 5-alkyl- or 5-hydroxyethyl triazones, aminotriazines, such as malamine, as well as the methylated derivatives of these condensates, poly(vic-epoxides) of aliphatic or aromatic types, alkyd resins, that is polyesters of polycarboxylic acids (for example phthalic, adipic, or sebacic) with a polyol (for example ethylene glycol, glycerol, trimethylolethane), and oil-modified types of alkyds containing from 25 to 60% of long chain fatty acid or ester (for example soybean oil). The content of these auxiliary materials may be from 1% to 35% by weight of the total weight of vinyl addition polymeric binder material.

When the thermosetting forms of the compositions of the present invention are used, the coating or impregnation may simply be dried at room temperature or whatever exterior temperature may prevail at the time as would be done with the simple thermoplastic types, reliance for development of cure being placed upon ageing for an extended period of time, for example several days, weeks, or in some cases, months. On the other hand, the cure of such films may be hastened by drying at elevated temperatures or heating at elevated temperatures (up to 200° C.) for several minutes to a ½ hour after drying at room temperatures.

Compositions of the present invention can be applied to a wide variety of materials, inclluding textiles, paper, leather, wood, masonry, ceramics, asbestos-cement shingles or siding, metal, and the like.

For making water-based paints typical formulations generally fall within the scope of the following tabulation which is tabulated on a solids basis:

| Material | Percent by Weight |
| --- | --- |
| Aqueous dispersed vehicle | 10 to 30 |
| Pigment composition | 1.5 to 55 |

-continued

| Material | Percent by Weight |
| --- | --- |
| Stabilizing and dispersing surfactants | 0.1 to 2.5 |
| Bodying or rheology control agents (for example, hydroxyethyl cellulose) | 0 to 2.0 |
| Anti-freeze agent, dry-time extender, and/or solvent (for example, propylene glycol, tributyl phosphate) | 0 to 10.0 |
| Anti-foam agent | 0 to 1.0 |
| Formaldehyde or formaldehyde-releasing agent | 0.08 to 0.4 |
| Isothiazolone | 0.02 to 1.0 |
| Ammonium hydroxide (28%), to make a pH of 7.5 to 10 | 0 to 1.5 |
| Water | Balance to make 100 |

The pigment volume concentration is preferably from 18% to 65%. The total of the dispersing and stabilizing surfactants is an amount no greater than 10% based on the weight of water-insoluble material in the binder.

The following examples are set forth to illustrate further this invention but are not intended to limit it in any way:

EXAMPLE 1

The following typical coating formulation is prepared

Formulation 1

| Materials | Pounds per 100 Gallons |
| --- | --- |
| Hydroxyethylcellulose (2.5% solution) | 85 |
| Water | 68.5 |
| Dispersing Agent (sodium salt of maleic anhydride - diisobutylene copolymer; 25% aqueous solution) | 15.0 |
| Wetting Agent (benzyl ether of tert-octyl phenoxypoly (20) ethoxyethanol) | 2.5 |
| Potassium tripolyphosphate | 1.5 |
| Antifoamer | 1.0 |
| Ethylene Glycol | 25.0 |
| Non-chalking Rutile $TiO_2$ | 250.0 |
| Extender (Talc) | 203.7 |
| The above materials are ground in a high speed mill at 3800 to 4500 feet/minute for 10 to 15 minutes, and let down, at a slower speed, as follows: | |
| Acrylic Vehicle - a 50% solids acrylic dispersion of a copolymer of about 60% ethyl acrylate, about 39% methyl methacrylate, and about 1% methacrylic acid, made by the procedure of Example 1 in U.S. Pat. No. 2,795,564, but unneutralized. | 390.8 |
| Long oil alkyd* | 30.8 |
| Antifoamer | 1.0 |
| Tributyl phosphate ⎫ | 8.8 |
| Propylene Glycol  ⎬ Premix | 35.0 |
| Isothiazolone** ⎭ | 2.0 |
| Water | 53.5 |
| Formaldehyde (37% Aqueous) | 4.0 |
| Base | 2.0 |

*Drier treated with 0.5% by weight of 6% cobalt, 0.5% of 6% manganese, and 1.4% of 24% lead, prior to incorporation of alkyd.
**2-n-octyl-3-isothiazolone or 5-chloro-2-n-octyl-3-isothiazolone.

After being neutralized with ammonium hydroxide, t-butylaminoethanol or dimethylaminoethanol to a pH of about 9.1 and stored at 140° F. for 10 days, this formulation shows essentially no chemical decomposition of the isothiazolone. When similar formulations containing no formaldehyde are stored under similar conditions, significant or complete decomposition of the isothiazolone occurs when the formulation has been neutralized to a pH of about 9 or higher. The formaldehyde-containing compositions also produce coatings having acceptable mildew resistance.

EXAMPLE 2

A coating formulation is prepared in which the acrylic vehicle of Formulation I is replaced with the polyblend acrylic vehicle described in Example 3 of U.S. Pat. No. 3,356,627. After being neutralized with ammonium hydroxide or dimethylaminoethanol to a pH of 9.0 and stored at 140° F. for 10 days, essentially no chemical decomposition of the isothiazolone is noticed. When similar formulations containing no formaldehyde are stored under similar conditions, significant or complete decomposition of the isothiazolone occurs.

EXAMPLE 3

The following semi-gloss coating formulation is prepared:

Formulation II

| Materials | Pounds per 100 Gallons |
| --- | --- |
| Propylene Glycol | 60.0 |
| Dispersing Agent (sodium salt of maleic anhydride-disobutylene copolymer; 25% aqueous | 14.9 |
| Antifoamer | 1.0 |
| Rutile $TiO_2$ | 275.0 |

The above materials are ground in a high speed mill at 3800 to 4500 feet/minute for 20 to 25 minutes, and let down, at a slower speed, as follows:

| | |
| --- | --- |
| Water | 70.0 |
| Acrylic Vehicle - polyblend acrylic vehicle of Example 3 of U.S. 3,356,627 | 546.7 |
| Antifoamer | 1.0 |
| Coalescent Aid (Texanol) Premix | 25.0 |
| 2-n-Octyl-3-isothiazolone | 2.0 |
| Propylene Glycol | 40.0 |
| Thickening Agent (3% Hydroxyethylcellulose) | 33.5 |
| Ammonium Hydroxide (28% Aqueous) | 2.0 |
| Formaldehyde (37% Aqueous) | 4.0 |

After being neutralized with ammonium hydroxide to a pH of about 8.9 and stored at 140° F. for 10 days, this formulation has good freeze-thaw stability and shows insignificant chemical decomposition of the isothiazolone. When similar formulations containing no formaldehyde are stored under similar conditions, significant or complete decomposition of the isothiazolone occurs. Coatings prepared from this formulation also exhibit good gloss.

EXAMPLE 4

This example shows the use of a compound which releases formaldehyde under basic conditions in place of formaldehyde itself in a typical coating formulation.

A coating formulation is prepared in which the formaldehyde is replaced with 4 pounds per 100 gallons of 1-(3-chloroallyl)-3,5,7-triaza-1-azoniaadamantane chloride and the formulation is neutralized with 4.0 pounds per 100 gallons of 28% aqueous ammonia. After storage for 10 days at 140° F., this formulation shows no significant chemical decomposition of the isothiazolone. When a similar formulation containing no quaternary salt is stored under similar conditions, significant or complete decomposition of the isothiazolone occurs.

EXAMPLE 5

The following coating formulations are prepared:

Formulation III

This formulation is similar to Formulation II, but as the vehicle has a 50% solids dispersion of copolymer of about 50% butyl methacrylate, about 49% methyl methacrylate, and about 1% methacrylic acid, prepared as described in U.S. Pat. No. 2,795,564.

Formulation IV

This formulation is similar to Formulation II, but the polyblend vehicle described in Example 1 of U.S. Pat. No. 3,356,627.

Formulation V

This formulation is similar to Formulation II, but has the polyblend vehicle described in Example 7(b) of U.S. Pat. No. 3,356,627.

Formulation VI

This formulation is similar to Formulation II, but has as the vehicle a 50% solids dispersion of the polymer described in Example 4 of U.S. Pat. No. 2,795,564.

In the above formulations, when formaldehyde is present, the formulation is stabilized against chemical decomposition of the 3-isothiazolone. However, when the formaldehyde is absent, significant decomposition of the isothiazolone occurs on prolonged storage. The formaldehydecontaining compositions also produce coatings having good mildew resistance.

EXAMPLE 6

Formulations are prepared in which the isothiazolone of Formulation I is replaced by:
(a) 2-n-hexyl-3-isothiazolone
(b) 2-t-butyl-3-isothiazolone
(c) 5-chloro-2-n-octyl-3-isothiazolone
(d) 2-(3,4-dichlorobenzyl)-3-isothiazolone
(e) 2-(p-chlorophenylethyl)-3-isothiazolone
(f) 3-isothiazolone
(g) 2-n-decyl-3-isothiazolone
(h) 2-benzyl-3-isothiazolone
(i) 5-chloro-2-methyl-3-isothiazolone
(j) 5-chloro-2-(4-chlorobenzyl)-3-isothiazolone
(k) 2-(4-chlorobenzyl)-3-isothiazolone
(l) 5-chloro-2-(2-phenylethyl)-3-isothiazolone
(m) 2-(2-phenylethyl)-3-isothiazolone In the above formulations, when formaldehyde or a compound which releases formaldehyde under basic conditions is present in the formulation, the formulation is stabilized against decomposition of the isothiazolone. However, when formaldehyde or formaldehyde-releasing agent is absent, decomposition of the isothiazolone occurs on storage.

It has also been found that formaldehyde and compounds which release formaldehyde stabilize organic solvent solutions of 3-isothiazolones, particularly solutions in polar organic solvents such as alcohols and glycols, especially at elevated temperatures. Generally, formaldehyde will stabilize solutions of 3-isothiazolones against chemical decomposition of the 3-isothiazolone when added at levels corresponding to about 2 to about 25%, preferably about 5 to about 20%, by weight of 37% aqueous formaldehyde.

EXAMPLE 7

This example shows the use of formaldehyde in stabilizing organic solvent solutions of 3-isothiazolones against chemical decomposition of the isothiazolone. To propylene glycol were added various levels of aqueous 37% formaldehyde and sufficient 2-n-octyl-3-isothiazolone to make a 45% by weight solution of the isothiazolone. After storage of the solutions for 30, 62, and 90 days at 140° F., the solutions were analyzed by gas-liquid chromatography to determine the loss in weight of active ingredient relative to the original sample. Three samples of the isothiazolone were used —Sample 1, a relatively impure sample (86.3% purity), Sample 2, a typical commercial grade sample (90.4%), and Sample 3, a highly pure sample (96.7%). Table I summarizes the results of these tests.

TABLE I

Chemical Stabilization of Isothiazolone Solutions With Formaldehyde

| Sample No. | Formaldehyde Level | % Decomposition (140° F) | | |
|---|---|---|---|---|
| | | 30 days | 62 days | 90 days |
| 1 | 0 | 10 | 22 | 41 |
| | 5 | 5 | 13 | 23 |
| | 10 | 4 | 9 | 11 |
| | 20 | 3 | 9 | 12 |
| 2 | 0 | 8.5 | 15 | 34 |
| | 5 | 4 | 10 | 18 |
| | 10 | 0 | 7 | 7 |
| | 20 | 2 | 7 | 10 |
| 3 | 0 | 1 | 6 | 13 |
| | 5 | 1 | 1 | 8 |
| | 10 | 1 | 0 | 2 |
| | 20 | 1 | 2 | 5 |

EXAMPLE 8

This example shows the use of formaldehyde in stabilizing paints containing the isothiazolone against chemical decomposition of the isothiazolone. Paints are prepared using Formulation I as in Example 1 employing dimethylaminoethanol for neutralization to a pH of about 9.1. Paints are made with and without formaldehyde and stored for 10 days at 140° F. By means of gas chromatography, the isothiazolone content is determined before and after storage. TABLE II gives the results which are obtained.

TABLE II

Formaldehyde Stabilization of Isothiazolone Containing Paints

| Y | R | R' | % Isothiazolone Remaining[1] in Paint[2] after 10 days at 140° F.[3] | |
|---|---|---|---|---|
| | | | DMAE[4] | DMAE[4]/HCHO[5] |
| n-C$_8$H$_{17}$ | H | H | 0 | 100 |
| n-C$_8$H$_{17}$ | H | Cl | 24 | 94 |
| n-C$_8$H$_{17}$ | Cl | Cl | 0 | 26 |
| -cyclohexyl | H | Cl | 36 | 51 |
| 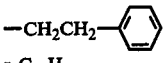 | CH$_3$ | Cl | 36 | 100 |
| t-C$_8$H$_{17}$ | Cl | Cl | 6 | 96 |
| n-C$_{10}$H$_{21}$ | H | H | 0 | 94 |
| n-C$_{10}$H$_{21}$ | H | Cl | 83 | 96 |
| n-C$_{10}$H$_{21}$ | Cl | Cl | 0 | 95 |
| —CH$_2$CH$_2$—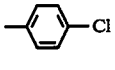 | H | Cl | 0 | 46 |
| n-C$_{12}$H$_{25}$ | H | H | 3 | 100 |
| n-C$_{12}$H$_{25}$ | H | Cl | 90 | 100 |
| n-C$_{12}$H$_{25}$ | Cl | Cl | 0 | 100 |
| 2-ethylhexyl | Cl | Cl | 0 | 87 |
| | H | H | 0 | 52 |

TABLE II-continued
Formaldehyde Stabilization of Isothiazolone Containing Paints

| Y | R | R' | % Isothiazolone Remaining[1] in Paint[2] after 10 days at 140° F.[3] | |
|---|---|----|------|------|
|   |   |    | DMAE[4] | DMAE[4]/HCHO[5] |
| —CH$_2$—⟨phenyl⟩ | H | H | 0 | 92 |
| —CH$_2$—⟨phenyl⟩—Cl | H | H | 0 | 95 |
| —CH$_2$—⟨phenyl⟩—Cl | H | Cl | 0 | 50 |

[1] Determined by gas-chromatography
[2] Same as Formulation I in Example 1 (page 15)
[3] Accelerated Storage Test Conditions
[4] 2 lb./100 gallons paint
[5] 4 lb./100 gallons paint
DMAE is dimethylaminoethanol
HCHO is formaldehyde It is to be understood that changes and variations may be made without departing from the spirit and scope of the invention as defined by the appended claims.

We claim:

1. In a coating composition which comprises a film-forming material, carrier, and a 3-isothiazolone, the improvement wherein the composition further comprises a stabilizing amount of formaldehyde.

2. The coating composition of claim 1 wherein the isothiazolone has the formula

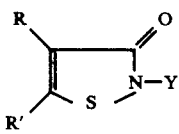

wherein
Y is a hydrogen atom, a (C$_1$-C$_{18}$)alkyl group, a (C$_6$-C$_{10}$)aryl group, or a (C$_7$-C$_{10}$) aralkyl group;
R is a hydrogen atom, a halogen atom, or a (C$_1$-C$_4$)alkyl group, and
R' is a hydrogen atom, a halogen atom, or a (C$_1$-C$_4$)alkyl group.

3. The composition of claim 1 which additionally comprises a pigment.

4. A method of stabilizing a coating composition which comprises a film-forming material, carrier, and a 3-isothiazolone against chemical decomposition of the isothiazolone which comprises incorporating into the composition a stabilizing amount of formaldehyde or a compound which releases formaldehyde under basic conditions.

5. The method of claim 4 wherein the 3-isothiazolone has the formula

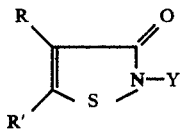

wherein
Y is a hydrogen atom, a (C$_1$-C$_{18}$)alkyl group, a (C$_6$-C$_{10}$)aryl group, or a (C$_7$-C$_{10}$)aralkyl group;
R is a hydrogen atom, a halogen atom, or a (C$_1$-C$_4$)alkyl group, and
R' is a hydrogen atom, a halogen atom, or a (C$_1$-C$_4$)alkyl group.

6. An article of manufacture comprising a substrate having a cured coating of the composition of claim 1.

7. The composition of claim 2 wherein the carrier is water and the film-forming material is an acrylic emulsion polymer.

8. The composition of claim 7 wherein the composition is neutralized to a pH of about 6.0 to about 9.2 with ammonia or an organic amine.

9. The composition of claim 8 wherein the formaldehyde is present in an amount equivalent to about 0.5 to about 20 pounds of 37% aqueous formaldehyde per 100 gallons of the composition, and the ammonia or organic amine is present in an amount of about 0.25 to about 10 pounds per 100 gallons of the composition.

10. A coating composition which comprises a film-forming acrylic emulsion polymer, water as a carrier, an isothiazolone of the formula

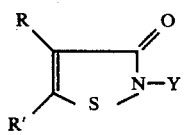

wherein
Y is a hydrogen atom, a (C$_1$-C$_{18}$) alkyl group, a (C$_6$-C$_{10}$)aryl group, or a (C$_7$-C$_{10}$)aralkyl group;
R is a hydrogen atom, a halogen atom, or a (C$_1$-C$_4$) alkyl group, and
R' is a hydrogen atom, a halogen atom, or a (C$_1$-C$_4$)alkyl group,
and formaldehyde in an amount equivalent to about 0.5 to about 20 pounds of 37% aqueous formaldehyde per 100 gallons of the composition, wherein the composition is neutralized to a pH of about 6.0 to about 9.2 with about 0.25 to about 10 pounds per 100 gallons of ammonia or an organic amine and wherein the isothiazolone is present in an amount of about 0.1 to about 20 pounds per 100 gallons of the composition.

11. The composition of claim 10 wherein Y is a hydrogen atom or an unsubstituted (C$_1$-C$_{18}$)alkyl group, R is a hydrogen atom, and R' is a hydrogen atom.

12. The composition of claim 11 wherein Y is a n-octyl group.

13. The composition of claim 10 wherein Y is a hydrogen atom or a (C$_1$-C$_{18}$)alkyl group, R is a hydrogen atom, and R' is a halogen atom.

14. The composition of claim 10 wherein Y is a 4-chlorobenzyl group, R is a hydrogen atom and R' is a hydrogen atom or a halogen atom.

15. The compoosition of claim 10 wherein the composition is neutralized to a pH of about 8.6 to about 9.1 with ammonia or dimethylaminoethanol.

16. The method of claim 5 wherein the carrier is water, the film-forming material is an acrylic emulsion polymer, and the composition is neutralized to a pH of about 6.0 to about 9.2 with ammonia or an organic amine.

17. The method of claim 16 wherein the formaldehyde or compound which releases formaldehyde is incorporated in an amount equivalent to about 0.5 to about 20 pounds of 37% aqueous formaldehyde per 100 gallons of the composition and wherein the composition is neutralized with about 0.25 to about 10 pounds of ammonia or organic amine per 100 gallons of the composition.

18. The method of claim 16 wherein the coating composition is neutralized to a pH of about 8.6 to about 9.1 with ammonia or dimethylaminoethanol.

19. The method of claim 4 which comprises incorporating into the composition a stabilizing amount of formaldehyde.

20. The method of claim 4 which comprises incorporating into the composition a compound which releases formaldehyde under basic conditions.

21. The method of claim 20 wherein the compound is 1-(3-chloroalkyl)-3,5,7-triaza-1-azoniaadamantane chloride.

* * * * *

UNITED STATES PATENT AND TRADEMARK OFFICE
CERTIFICATE OF CORRECTION

PATENT NO. : 4,129,448

DATED : December 12, 1978

INVENTOR(S) : John A. Dupont et al

It is certified that error appears in the above-identified patent and that said Letters Patent are hereby corrected as shown below:

Column 6, line 59 - Change "inclluding" to read - -including- -

Column 9, line 28 - Change "formaldehydecontaining" to read
- -formaldehyde-containing- -

Column 10, line 54 - Table II Under Heading DMAE$^4$ - Change "36" first occurrence to read -- -0- --.

Signed and Sealed this

Sixth Day of November 1979

[SEAL]

Attest:

RUTH C. MASON
Attesting Officer

LUTRELLE F. PARKER
Acting Commissioner of Patents and Trademarks